United States Patent
Zimdars (10) Patent No.: US 8,436,310 B2
(45) Date of Patent: May 7, 2013

(54) SYSTEM AND METHOD REDUCING FIBER STRETCH INDUCED TIMING ERRORS IN FIBER OPTIC COUPLED TIME DOMAIN TERAHERTZ SYSTEMS

(75) Inventor: David Zimdars, Ann Arbor, MI (US)

(73) Assignee: Picometrix, LLC, Ann Arbor, MI (US)

( * ) Notice: Subject to any disclaimer, the term of this patent is extended or adjusted under 35 U.S.C. 154(b) by 0 days.

(21) Appl. No.: 13/266,023

(22) PCT Filed: Apr. 27, 2010

(86) PCT No.: PCT/US2010/032534
§ 371 (c)(1),
(2), (4) Date: Mar. 27, 2012

(87) PCT Pub. No.: WO2010/126872
PCT Pub. Date: Nov. 4, 2010

(65) Prior Publication Data
US 2012/0175520 A1   Jul. 12, 2012

Related U.S. Application Data

(60) Provisional application No. 61/173,192, filed on Apr. 27, 2009.

(51) Int. Cl.
*G01J 5/02* (2006.01)
*G02B 6/26* (2006.01)

(52) U.S. Cl.
USPC .............. 250/341.1; 250/338.1; 385/15

(58) Field of Classification Search ........... 250/338.1, 250/338.4, 341.1, 341.8; 385/15, 24, 27
See application file for complete search history.

(56) References Cited

U.S. PATENT DOCUMENTS 5,630,003 A * 5/1997 Arroyo ............................ 385/113
6,320,191 B1 * 11/2001 Rudd ............................ 250/341.1

* cited by examiner

*Primary Examiner* — Mark R Gaworecki
(74) *Attorney, Agent, or Firm* — Brinks Hofer Gilson & Lione (57) ABSTRACT

A system for reducing effects relating to stretching of an optical fiber includes an optical control source, the optical source outputting an optical signal, a terahertz transmitter and receiver both being optically coupled to the optical source, and a means for providing the optical signal to both the terahertz transmitter and terahertz receiver such that the terahertz receiver is synchronized to the terahertz transmitter by the optical signal. The means prevents the stretching of an fiber carrying the optical signal provided to the terahertz transmitter or terahertz receiver or allows for the stretching an optical fiber such that the terahertz receiver will still be synchronized to the terahertz transmitter by the optical signal.

15 Claims, 6 Drawing Sheets

SYSTEM AND METHOD REDUCING FIBER STRETCH INDUCED TIMING ERRORS IN FIBER OPTIC COUPLED TIME DOMAIN TERAHERTZ SYSTEMS

BACKGROUND

1. Field of the Invention

The invention relates to terahertz generation systems and more particular to terahertz generation systems having a pump-probe configuration.

2. Description of the Known Art

Time-domain terahertz generation systems employ terahertz generation and receiver devices which are triggered and powered by laser pulses of sub 300 femtosecond durations. The terahertz devices generate and/or detect electromagnetic pulses or pulse sequences with a Fourier transform possess spectral content in the 0.020 to >10 terahertz range. Most commonly these terahertz electromagnetic pulses are near single cycle sub-picosecond transients in the 0.050 to 4 terahertz range.

There are several common terahertz transmitter and receiver devices which are used in a pump-probe configuration. These include non-linear electro-optic crystals (such as ZnTe, GaP and others) and photoconductive semiconductor devices ("Auston Switches," fabricated on GaAs, InGaAs, and other ultra high-speed semiconductors). A chief difference among these is the center wavelength of the optical drive in the pump-probe apparatus (GaAs approx. 800 nm and InGaAs between 1000 and 1600 nm, for example). For illustration purposes, photoconductive devices will be discussed. In a photoconductive terahertz transmitter, a bias photoconductive switch gap is illuminated by the femtosecond laser pulse. Carriers are generated and a current flows across the bias gap, quickly rising with the temporal profile of the excitation laser pulse, and quickly falling with the recombination of the carriers. This time varying current creates the terahertz pulse through Maxwell's equations.

The generated terahertz pulse electromagnetic field is detected by a method of highly precise time gating, usually referred to as a pump-probe method. The first laser pulse which drives the terahertz transmitter is the pump. A second laser pulse, precisely time delayed with femtosecond or sub-femtosecond precision with respect to the first terahertz transmitter pulse is the probe, as illustrated in U.S. Pat. Nos. 6,320,191 and 6,849,852; the entirety of both is hereby incorporated by reference. The probe pulse illuminates an un-biased photoconductive switch. The switch can carry current for sub-picosecond duration. If the femtosecond laser pulse driving the terahertz receiver is time coincident with a portion of the generated terahertz pulse electromagnetic field, current will flow across the switch. The current is proportional to the amplitude and sign of the terahertz pulse field at that particular time. Typically, the timing between the pump and the probe is systematically varied and the time-domain terahertz waveform is recorded as a function of terahertz receiver current vs. the delay between the pump and the probe.

Regardless of the terahertz transmitter or receiver device employed in the pump-probe apparatus, the optical path length of the pump beams and probe beams must be known and kept stable to femtosecond or sub-femtosecond precision. If the path length is not stable, this can introduce short term jitter or long term timing drift. This timing error will distort the measured terahertz wave form in a number of ways. For example, the Fourier transform and a time domain terahertz spectroscopy measurement will have power distributed to incorrect frequencies. In another example, the jitter and drift will distort the time of flight of the terahertz pulse through materials such as paper, resulting in incorrect thickness measurement derived from the terahertz post timing.

In previous implementations, time domain terahertz instrumentation would deliver the pump and probe beams entirely in a free space environment. This free space environment's stability is entirely dependent on the mechanical stability of the optical transport. However, because of this dependence, free space transport is a highly restrictive implementation. The femtosecond laser providing the optical pump and probe, as well as the optical delay mechanism must be permanently attached to the same mechanical structure holding the terahertz transmitter and receiver devices. These terahertz transmitter and receiver devices are not freely positionable with respect to each other and the other components of the system without disassembling the system and then reassembling the entire system in a new position.

Freely positionable terahertz transmitter and receiver modules can be constructed by delivering the pump and probe femtosecond optical drive through optical fibers. The optical fibers are typically single mode, or single mode polarization maintaining. The fibers allow the terahertz transmitter and receiver modules to be moved together or independently during instrument configuration or while the instrument is in use (for example, the transmitter and receiver can be mounted in a raster scan imaging gantry—this allows the object under test to remain stationary; a free space system usually would require the object to move while the free space terahertz system remains stationary). The fibers guide the pump and probe optical drive as the fiber bends, as well as mostly, but often times insufficiently maintain a constant optical path length in both the pump and probe optical path. As long as the motion of the fibers consists of simple bending which does not stretch or put the fibers under tension, the optical path length remains constant. Unfortunately, it is possible that motion of the optical fibers during the pump and probe procedure can be inadvertently stretched during motion. This can occur by simple tension or through the bending and other motions which cause the optical fibers to bind within the cable jacket, bulkhead, or other locations which induces tension and stretching.

The pump and/or probe pulse group travel time through the optical fibers will increase if the optical fibers are stretched and/or tensioned. This group delay results through one or more physical effects, chiefly increase in the length dimension of the fiber core, and/or strain induced changes in the group velocity, which is related by the first derivative of the index of refraction verses frequency. These unintentional delays of several picoseconds which may result from stretching or tensioning the optical fibers may severely distort the time domain terahertz waveform generated and/or detected by the pump-probe method.

BRIEF SUMMARY

In an effort to overcome the drawbacks of the prior art, a system for reducing effects relating to stretching of an optical fiber is described. The system includes an optical control source, the optical source outputting an optical signal, a terahertz transmitter and receiver both being optically coupled to the optical source, and a means for providing the optical signal to both the terahertz transmitter and terahertz receiver such that the terahertz receiver is synchronized to the terahertz transmitter by the optical signal. The means prevents the stretching of the fibers propagating the optical signal provided to the terahertz transmitter or terahertz receiver; or provides a method of propagating the transmitter and receiver optical pulses such that the optical path length in each of the paths providing the optical signal to the terahertz transmitter and terahertz receiver are stretched substantially equally.

In the case where the stretching of the fibers is prevented; the means for providing the optical signal may be a flexible tubular structure having a first end and a second end, the flexible tubular structure having wall portions defining an inner space. The first end of the flexible tubular structure is coupled to the optical control source, while the second end is coupled to the terahertz receiver and/or transmitter. This embodiment also includes at least one optical fiber having a first end optically coupled to the optical source and a second end optically coupled to either the terahertz receiver or the terahertz transmitter. The optical fiber passes though the inner space of the flexible tubular structure. The optical fiber is routed through the tubular structure in a manner such that tension on the tubular structure does not stretch or induce tension on the fiber; and that bending on the tubular structure simply bends the fiber, and does not inadvertently induce stretching or tension on the fiber as the tubular structure is itself bent and moved. This can be accomplished by using an optical fiber with a length that is longer than the flexible tubular structure. Moreover, if the length of the optical fiber is longer than the flexible tubular structure when stretched, any stretching of this flexible tubular will not stretch the optical fiber.

In the case where the optical paths through the fiber are stretched substantially equally, the means for providing the optical signal may be an optical fiber having a first core and a second core. The optical fiber has a first end optically coupled to the pump probe apparatus optical source. The first core of the optical fiber is optically coupled to the terahertz transmitter (pump path), while the second core of the optical fiber is optically coupled to the terahertz receiver (probe path). In the event this optical fiber is stretched or tensioned, any optical signals traveling though the two cores of the fiber will be stretched by the same amount, negating any effects caused when only one core of a single optical fiber is stretched.

In yet another embodiment in the case where the optical paths through the fiber are stretched substantially equally, the means for providing the optical signal may be a single optical fiber with a single core. This single optical fiber is optically coupled to an optical source and the terahertz transmitter and receiver. In this embodiment, signals provided to terahertz transmitter and receiver is sent down the optical fiber orthogonal to each other. These signals can then be demultiplexed and provided to the terahertz transmitter and receiver. The optical fiber may be polarization maintaining, in which case the pump/transmitter optical signal and the probe/receiver optical signal may be multiplexed and demultiplexed by launching and then separating orthogonal polarizations of light. In another possibility, the pump/transmitter optical signal and the probe/receiver optical signal may have substantially optical center frequencies and the signals may be multiplexed and demultiplexed through the use of frequency band pass filters. Since only a single fiber is utilized, any stretching of this fiber will stretch both optical signals by the same amount, negating any effects if only one optical signal is stretched.

Further objects, features and advantages of this invention will become readily apparent to persons skilled in the art after a review of the following description, with reference to the drawings and claims that are appended to and form a part of this specification.

DETAILED DESCRIPTION OF THE DRAWINGS AND THE PRESENTLY PREFERRED EMBODIMENTS

Figure 1:
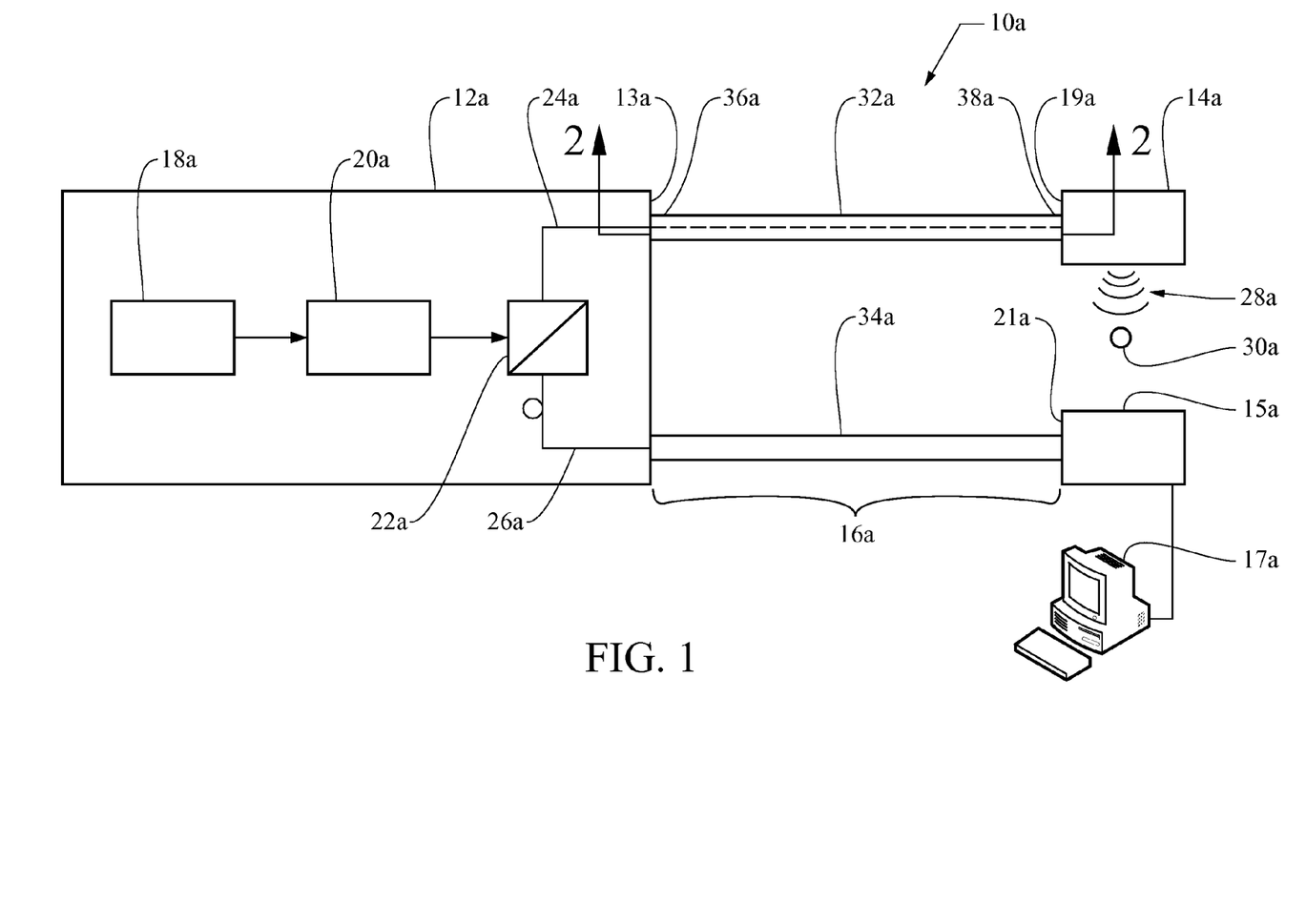
FIG. 1 illustrates a first embodiment of a system for reducing effects relating to stretching of an optical fiber utilizing two flexible tubular structures.

Referring to FIG. 1, a system 10a for reducing effects relating to the stretching of an optical fiber is shown. As its primary components, the system 10a includes an optical control source 12a, a terahertz transmitter 14a, a terahertz receiver 15a and a means 16a for providing optical signals outputted by the optical control source 12a to both the terahertz transmitter 14a and a terahertz receiver 15a. The means 16a for providing the optical signal is such that the terahertz receiver 14a is synchronized to the terahertz transmitter 14a by optical signals emitted by the optical control source 12a. Additionally, the means 16a prevents the stretching of the optical signals provided to the terahertz transmitter 14a and the terahertz receiver 15a or stretches optical signals from by the optical control source 12a such that the optical signals provided to the terahertz transmitter 14a are substantially equal to the optical signals provided to the terahertz receiver 15a.

Generally, the optical control source 12a may take a variety of different embodiments. In one such embodiment, the optical control source 12a includes a laser source 18a configured to output optical pulses. Generally, the laser source 18a produces femtosecond output pulses. Optically coupled to the laser source 18a is a compensator 20a. Optical pulses emitted by the laser source 18a are provided to the compensator 20a which adds opposite sign dispersion to the optical pulses to correct for a stretching of the optical pulses as they travel through the means 16a. The compensator 20a and laser source 18a may be optically coupled to each other by an optical fiber or may be optically coupled to each other in a free space manner.

Once the appropriate amount of opposite sign dispersion is provided to the optical pulses by the compensator 20a, the optical pulses are provided to a splitter 22a. The splitter 22a splits the optical pulses and provided them to a first optical fiber 24a and a second optical fiber 26a. In this embodiment, the first optical fiber 24a is a single mode fiber wherein pulses split by the splitter 22a are provided to the optical fiber 24a. In like matter, the second optical fiber 26a is also an optical fiber receiving pulses split from the splitter 22a.

The optical fiber 24a is coupled to the terahertz transmitter 14a. Similarly, optical fiber 26a is optically coupled to terahertz receiver 15a. When the terahertz transmitter 14a receives these optical pulses from the optical fiber 24a, the terahertz receiver will output terahertz radiation 28a to a sample 30a. When the terahertz receiver 15a receives optical pulses from the optical fiber 26a, the optical receiver will receive the radiation 28a emitted from the terahertz transmitter 14a. Because of this, timing is incredibly important such that the terahertz receiver 15a is synchronized to the terahertz transmitter 14a by the optical pulses traveling on optical fiber 24a and optical fiber 26a. Because of this synchronization, any stretching of the optical fibers 24a and 26a that is not appropriately compensated for or prevented, can interfere with this timing preventing terahertz radiation 28a from being transmitted or received at the appropriate time interval. The means 16a in this embodiment will eliminate any stretching or tensioning of the optical fibers 24a and 26a.

Once the radiation 30a is received by the terahertz receiver 15a, terahertz receiver 15a generates an electrical signal which can be interpreted, scaled and/or digitized by a data acquisition system 17a. The data acquisition system 17a is generally electrically coupled to the terahertz receiver 15a.

Figure 2:
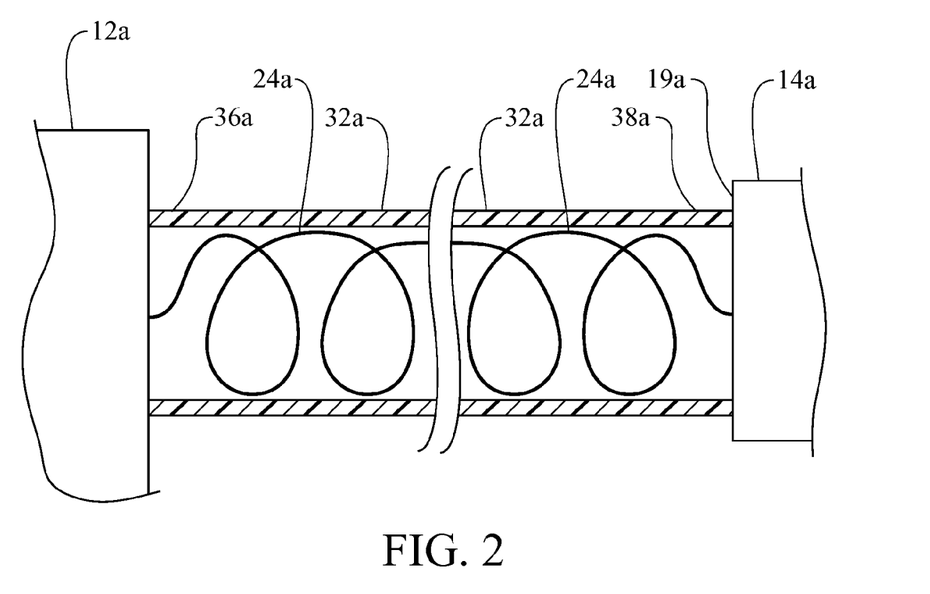
FIG. 2 is a more detailed view of the flexible tubular structure of FIG. 1 taken generally along lines 2-2 of FIG. 1.

The means 16a includes a flexible tubular structure 32a having a first end 36a and a second end 38a. The first end 36a is coupled to the housing 13a of the optical control unit 12a. The flexible tubular structure 32a houses a portion of the optical fiber 24a in an interior space. As best shown in FIG. 2, which is a cutout of the flexible tubular structure 32a generally taken along lines 2-2 of FIG. 1, the flexible tubular structure 32a is of a length that is shorter than the length of the optical fiber 24a located within the interior space of the flexible tubular structure 32a. A second end 38a of the flexible tubular structure 32a is then coupled to the housing 19a of the terahertz transmitter 14a.

The flexible tubular structures 32a and 34a are usually a flexible plastic conduit of inside diameter several times larger than the outside diameter of the optical fibers 24a and 26a. The fibers 24a and 26a is wound spiral fashion onto a line, and the line is used to pull the fibers 24a and 26a through the flexible tubular structures 32a and 34a. Pushing on to each end of the fiber expands the spiral up against the inside of the flexible tubular structures 32a and 34a. The inside of the flexible tubular structures 32a and 34a may have a surface which maintains the spiral, yet does not bend as the flexible tubular structures 32a and 34a are bent.

The flexible tubular structure 32a is made such that it will not stretch further than the unstretched portions of the optical fiber 24a located within the interior space of the flexible tubular structure 32a. Since the portions of the optical fiber 24a located between the first end 36a and the second end 38a the flexible tubular structure 32a are longer than the length of the flexible tubular structure, any stretching of the flexible tubular structure will not result in a stretching of the optical fiber 24a as the optical fiber 24a is longer than the length of the flexible tubular structure 32a. By so doing, the fiber 24a will not be stretched in portions located within the flexible tubular structure 32a, thereby preventing any stretching of fiber and disruption of the synchronization of the terahertz transmitter 14a and the terahertz receiver 15a. In like manner, the flexible tubular structure 34a containing optical fiber 26a is constructed in a similar fashion as the flexible tubular structure 32a as shown and described in FIG. 2 and the previous paragraphs.

Figure 3:
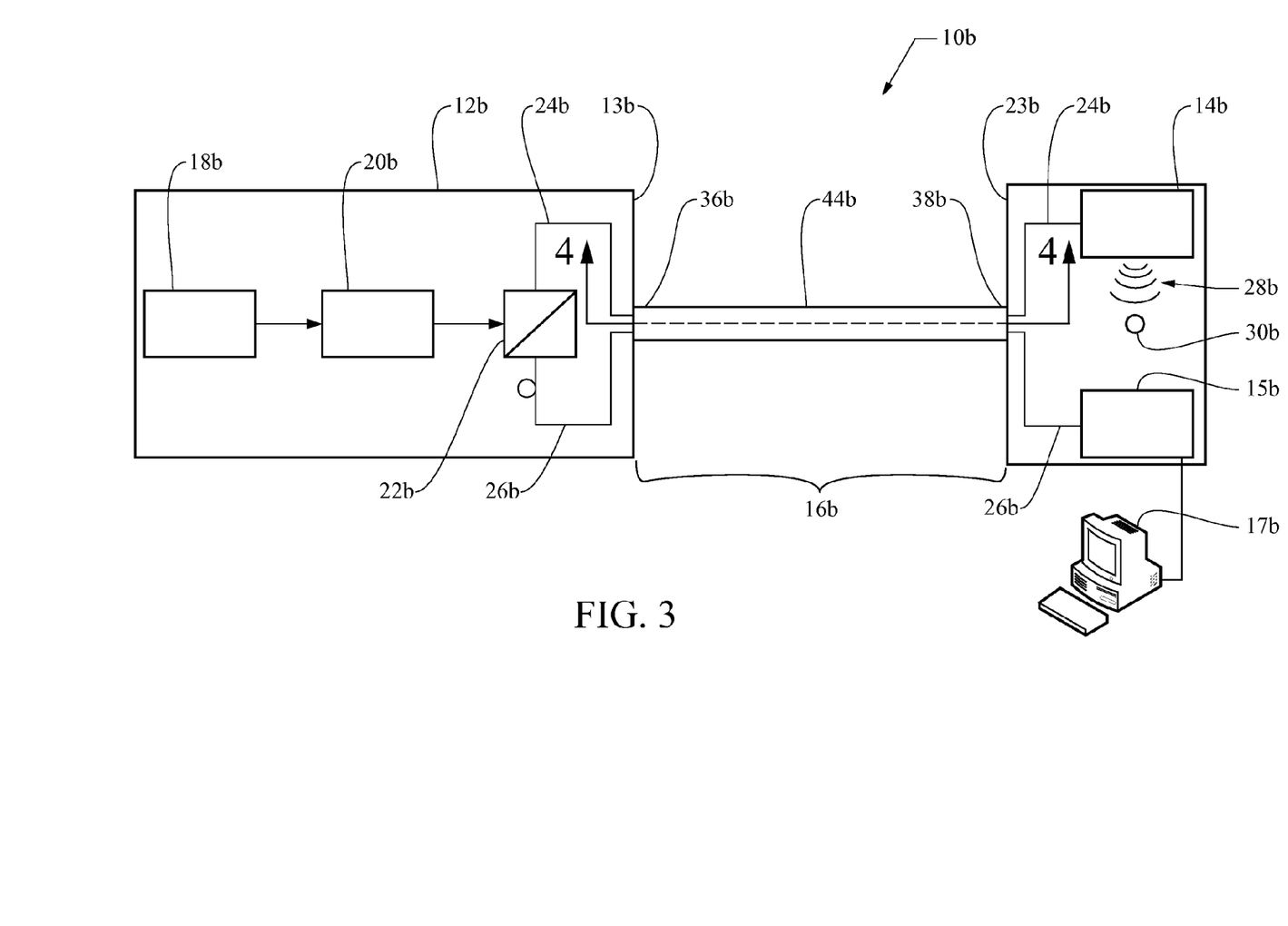
FIG. 3 illustrates a second embodiment of a system for reducing effects relating to stretching of an optical fiber utilizing an optical fiber having a single flexible tube.

Referring to FIG. 3, another embodiment of the system 10b is shown. In this embodiment, like reference numerals are used to refer to like elements previously described with the exception that the letter "b" has been appended on to each element number.

Figure 4:
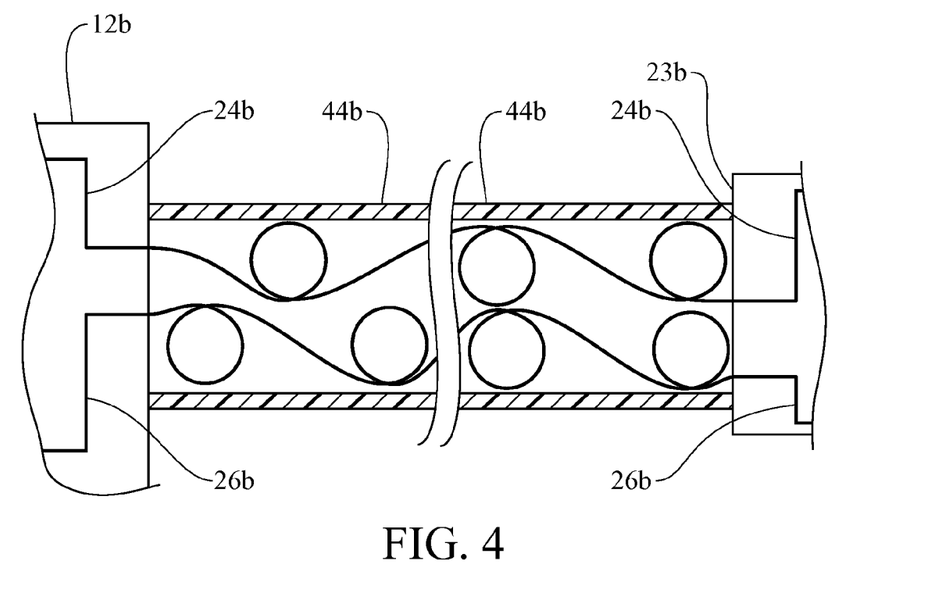
FIG. 4 is a more detailed view of the single flexible tube in FIG. 3 generally taken along lines 4-4 of FIG. 3.

In this embodiment, the means 16b includes a single flexible tubular structure 44b. A more detailed view of the flexible tubular structure 44b is shown in FIG. 4 and generally taken along lines 4-4 of FIG. 3. The flexible tubular structure 44b has a first end 36b and a second end 38b. The first end is coupled to the housing 13b of the optical control unit 12b, while the second end 38b is coupled to a housing 23b containing the terahertz transmitter 14b and terahertz receiver 15b. Located within the interior space of the flexible tubular structure 44b are optical fibers 24b and 26b.

The lengths of the optical fibers 24b and 26b enclosed within the flexible tubular structure 44b are longer than the length of the flexible tubular structure 44b. Any stretching or tension placed on the flexible tubular structure 44b will be such that it will not stretch or tension the optical fibers 24b and 26b. By so doing, any stretching of the optical fibers 24b and 26b is eliminated.

Figure 5:
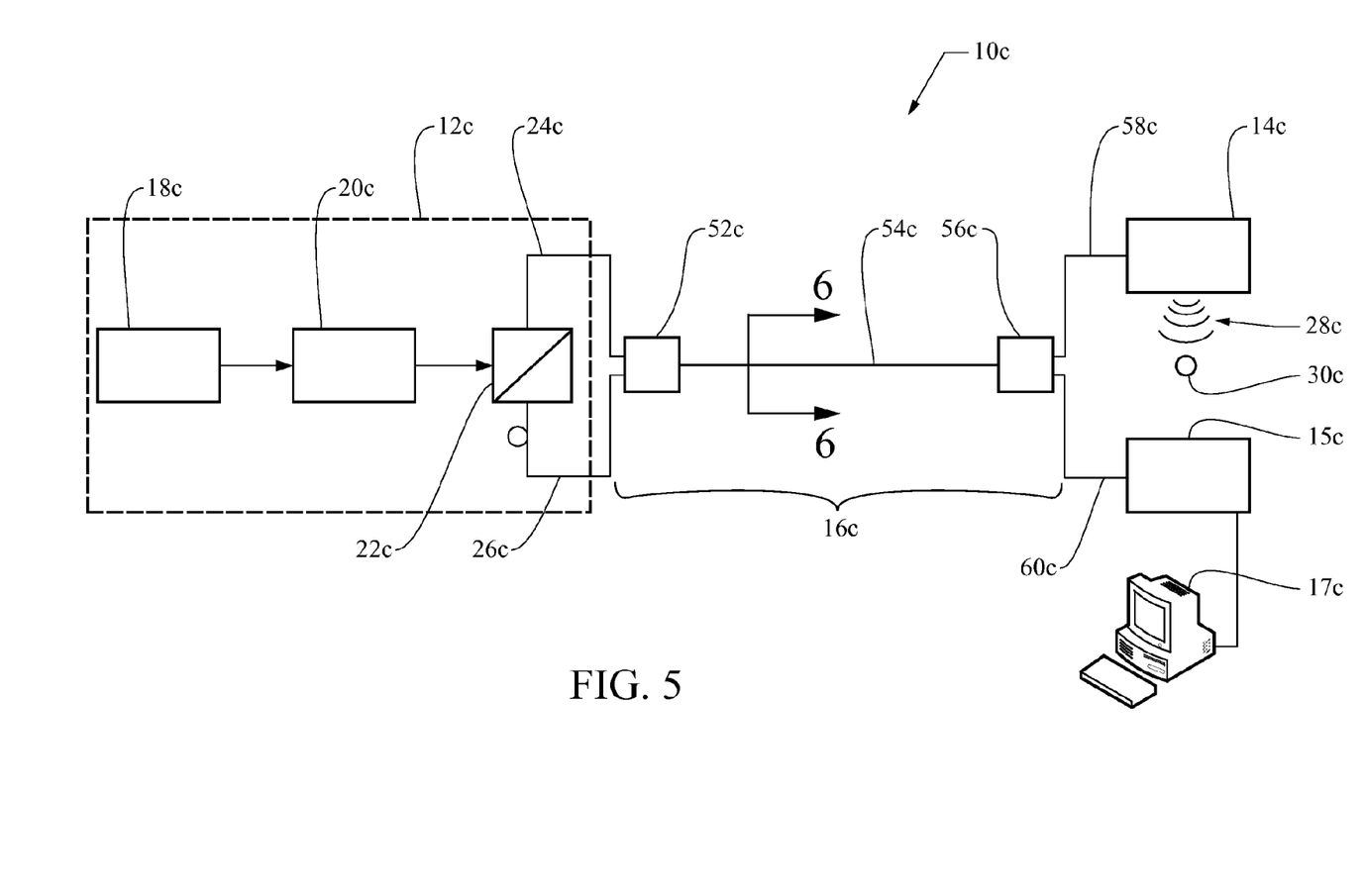
FIG. 5 illustrates a third embodiment of a system for reducing effects relating to stretching of an optical fiber having an optical fiber with two cores.

Referring to FIG. 5, another embodiment of the system 10c is shown. In this embodiment, like reference numerals are used to refer to like elements previously described with the exception that the letter "c" has been appended on to each element number. Like before, the laser source 18c emits optical pulses to a compensator 20c. The compensator 20c then outputs these compensated pulses to compensate for any dispersion that may occur in the system 10c to splitter 22c. Splitter 22c splits the optical signal into two optic paths along optical cable 24c and optical cable 26c.

However, the means 16c includes a dual core fiber optical multiplexer 52c receiving optical signals from optical cables 24c and 26c. The optical multiplexer 52c multiplexes the optical signals coming from optical cables 24c and 26c and provides them to a dual core optical fiber 54c. The dual fiber optical multiplexer 52c takes either the output from two independent free-space optical beams; or two independent fiber optics (in either case one for the pump/transmitter and the other for the probe/receiver) and couples them into two cores within the same optical fiber. The coupling may take place through an imaging optic or a fused fiber optic tapered beam combiner.

Figure 6:
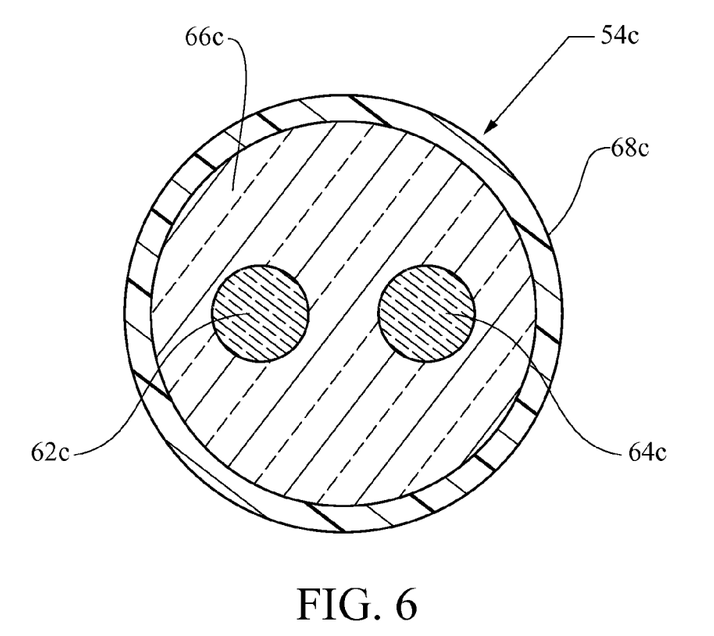
FIG. 6 is a more detailed view of the optical fiber having two cores in FIG. 5 generally taking along lines 6-6 FIG. 5.

Referring to FIG. 6, a more detailed view of the dual core optical fiber 54c, generally taken along lines 6-6 of FIG. 5 is shown. The dual core optical fiber 54c includes a first core 62c and a second core 64c for transmitting the optical signal emitted from the optical cables 24c and 26c, respectively. Surrounding the dual cores 62c and 64c is a cladding 66c. Surrounding the cladding 64c is a buffer 68c. Similar to single mode fibers, a dual core fiber transmits optical signals via the core 62c and 64c by utilizing the properties of total internal reflection. The two cores are sufficiently separated such that they do not couple light between them.

Referring back to FIG. 5, the optical signals traveling along the dual core optical fiber 54c are received by an optical demultiplexer 56c which then transmits the optical signals to the terahertz transmitter 14c and the terahertz receiver 15c via optical cables 56c and 60c, respectively. The dual core demultiplexer reverses the action of the multiplexer, by either imaging the two cores onto independent free space paths or through the use of a fused fiber optic tapered fiber beam splitter which re-establishes two independent fiber paths. In the event the dual core optical fiber 54c is stretched or tensioned, any optical signals traveling though the two cores 62c and 64c will be stretched by the same amount, negating any effects caused when only one core of a single optical fiber is stretched.

Figure 7:
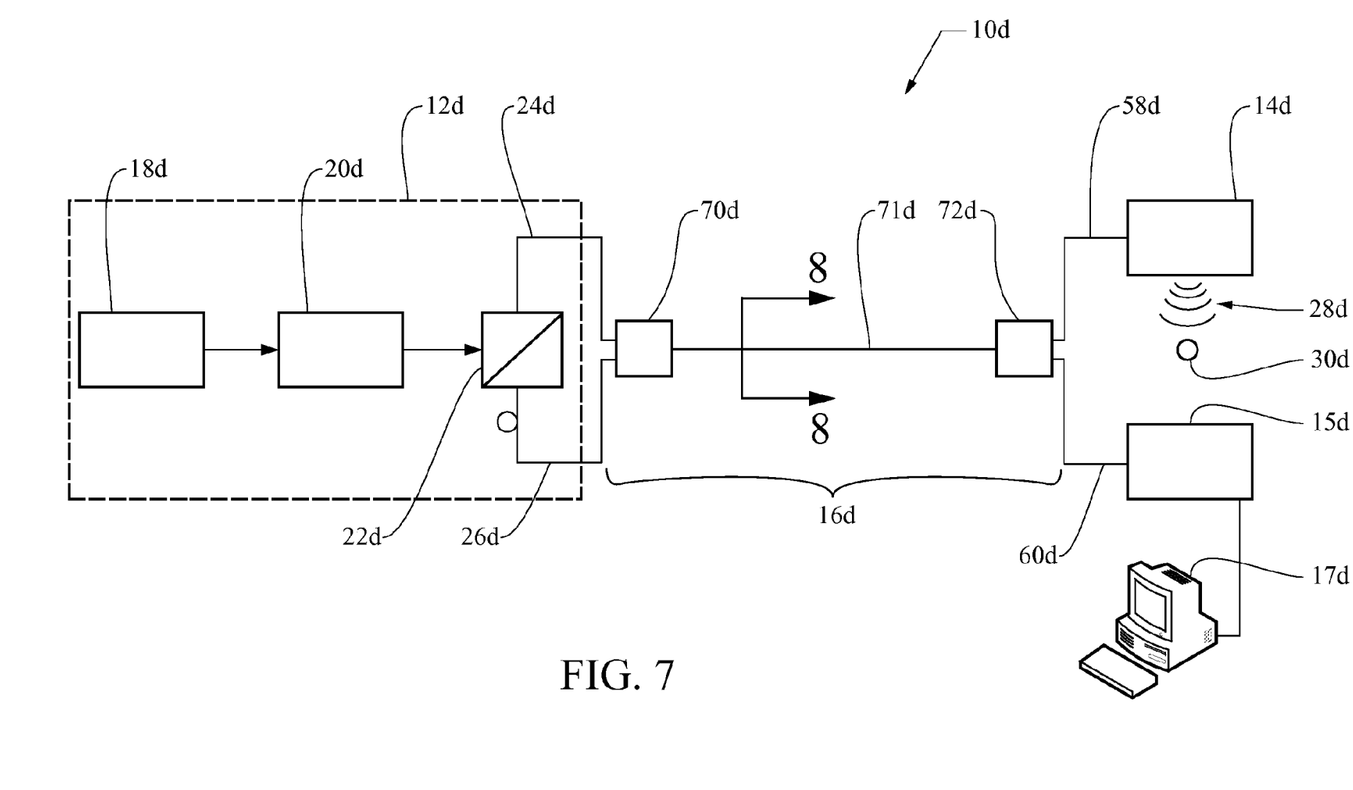
FIG. 7 illustrates a fourth embodiment of a system for reducing effects relating to stretching of an optical fiber utilizing a single optical fiber configured to transport a multiplexed optical signal.

Referring to FIG. 7, another embodiment of the system 10d is shown. In this embodiment, like reference numerals are used to refer to like elements previously described with the exception that the letter "d" has been appended on to each element number. In this embodiment, optical signals emitted by the splitter 22d are provided to optical cables 24d and 26d.

Optical cables 24*d* and 26*d* are optically coupled to an single core fiber optical multiplexer 70*d*. The single core optical multiplexer 70*d* provides the signals from the optical cables 24*d* and 26*d* to the optical fiber 71*d*. Either polarization multiplexing or frequency multiplexing may be used to combine the pump/transmitter and probe/receiver optical signal onto a single fiber optic core. In the case of polarization multiplexing, polarization maintaining fiber is used, and the multiplexer consists of a free space or fiber optic polarization beam combiner which launches the pump/transmitter optical signal and the probe/receiver optical signal onto the orthogonal optical polarizations of the same polarization maintaining fiber. In the case of frequency multiplexing, the pump/transmitter optical signal and the probe/receiver optical signal have sufficiently different optical center frequencies such that a dichroic beam combiner can be used to combine the optical signal onto the same path or fiber.

Figure 8:
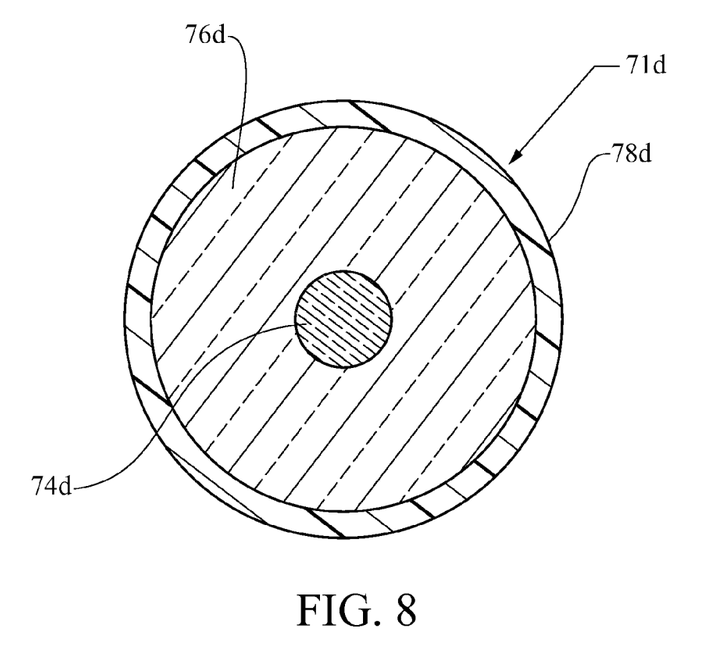
FIG. 8 is a more detailed view of the optical fiber illustrated in FIG. 7 generally taken along lines 8-8 of FIG. 7.

Referring to FIG. 8, optical fiber 71*d* is generally a single mode optical fiber having a core 74*d*, a cladding 76*d* and a buffer 78*d*. If a polarization multiplexer is used the optical fiber must also be polarization maintaining, and has stress applying parts (not shown) which induce birefringence in the fiber, which allow a fast polarization axis and an orthogonal slow polarization axis. As it is well understood, optical signals travel down the core 74*d* of the optical fiber 71*d* via total internal reflection. However, in this embodiment, the optical multiplexer 70*d* sends one optical signal from one of the optical cables 24*d* and 26*d* either in one pure orthogonal polarization state or in one unique frequency band with respect to the other signal pure polarization state or unique frequency band from the optical cable 24*d* or 26*d* down the single core 74*d* of the optical fiber 71*d*.

Referring back to FIG. 7, the orthogonal signal sent on the optical fiber 71*d* is received by an optical demultiplexer 72*d* which demultiplexes these two signals and sends one of the signals to optical fiber 58*d* and the other signal to optical fiber 60*d*. In the case of polarization multiplexing, a polarizing beam splitting optic or fiber optic coupler is used to separate the pump/transmitter optical signal from the probe/receiver optical signal. In the case of frequency multiplexing, a dichroic beam splitter or frequency band-pass filters are used to separate the pump/transmitter optical signal from the probe/receiver optical signal. In turn these signals are then provided to the terahertz receiver 15*d* and the terahertz transmitter 14*d*.

As such, because the signals are sent down the same optical fiber 71*d*, any stretching of the optical fiber 71*d* will impact the signals sent along the optical fiber 71*d* in an equal manner. Because of this, any distortion caused by the stretching will be compensated for each other as both signals will be stretched and both signals will therefore be received by the terahertz receiver and terahertz transmitter at the same relative times determined by the intended pump and probe timing regardless of the motion of the fiber. As long as these signals are received by the terahertz transmitter and terahertz receiver at the same relative times determined by the intended pump and probe timing, any stretching of the optical cable 71*d* will be compensated for and therefore will not cause any related errors.

The above disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

The invention claimed is:

1. A system for reducing effects relating to stretching of an optical fiber, the system comprising:
    an optical source, the optical source outputting an optical signal;
    a terahertz transmitter optically coupled to the optical source, the terahertz transmitter configured to emit terahertz radiation to a sample when activated by the optical signal;
    an terahertz receiver optically coupled to the to the optical source, the terahertz receiver configured to detect terahertz radiation conditioned by the sample and generate an electrical signal which can be interpreted, scaled and/or digitized by a data acquisition system electrically coupled to the terahertz receiver;
    a means for providing the optical signal to both the terahertz transmitter and terahertz receiver such that the terahertz receiver is synchronized to the terahertz transmitter by the optical signal; and
    wherein the means is configured to prevent the stretching or bending of a first optical fiber carrying the optical signal provided to the terahertz transmitter or terahertz receiver.

2. The system of claim 1, wherein the means further comprises:
    a flexible tubular structure having a first end and a second end, the flexible tubular structure having wall portions defining an inner space;
    wherein the first end of the flexible tubular structure is coupled to a housing of the optical control source and the second end of the flexible tubular structure is coupled to a housing of either the terahertz receiver or terahertz transmitter;
    the first optical fiber having a first end optically coupled to the optical control source and a second end optically coupled to either the terahertz receiver or the terahertz transmitter, wherein the first optical fiber passes though the inner space of the flexible tubular structure;
    wherein the length of the first optical fiber between the first and second ends of the flexible tubular structure is longer than the length of the flexible tubular structure.

3. The system of claim 2, wherein the first optical fiber is coupled to the terahertz receiver.

4. The system of claim 2, wherein the first optical fiber is coupled to the terahertz transmitter.

5. The system of claim 2, further comprising:
    a second optical fiber, the second optical fiber having a first end optically coupled to the optical source and a second end optically coupled to either the terahertz receiver or the terahertz transmitter, wherein the second optical fiber passes though the inner space of the flexible tubular structure;
    wherein the length of the second optical fiber between the first and second ends of the flexible tubular structure is longer than the length of the flexible tubular structure.

6. The system of claim 1, wherein optical source further comprises a laser source configured to output optical pulses.

7. The system of claim 6, further comprising a compensator optically located between the laser source and the means for providing the optical signal to both the terahertz transmitter and terahertz receiver, wherein the compensator is configured to add opposite sign dispersion to optical pulses emitted by the laser source to correct for a stretching of the optical pulses as they travel through the means for providing the optical signal to both the terahertz transmitter and terahertz receiver.

8. The system of claim 7, further comprising an optical splitter optically located between the laser source and the means for providing the optical signal to both the terahertz transmitter and terahertz receiver, wherein the optical splitter is configured to spilt the optical signal and provide the split optical signals to the means for providing the optical signal to both the terahertz transmitter and terahertz receiver.

9. The system of claim 8, wherein the means further comprises:
an optical fiber having a first core and a second core;
the optical fiber has a first end optically coupled to the optical source;
the first core of the optical fiber being optically coupled to the terahertz transmitter; and
the second core of the optical fiber being optically coupled to the terahertz receiver.

10. The system of claim 9, further comprising:
a multiplexer located optically between the optical source and the optical fiber, the multiplexer being configured to send the optical signal via the first core and the second core of the optical fiber; and
a demultiplexer located optically between the optical fiber and the terahertz receiver and terahertz transmitter, the demultiplexer being configured to provide the optical pulse from the first core to the terahertz receiver and provide the optical pulse from the second core to the terahertz transmitter.

11. A system for reducing effects relating to stretching of an optical fiber, the system comprising:
an optical source, the optical source outputting an optical signal;
a terahertz transmitter optically coupled to the optical source, the terahertz transmitter configured to emit terahertz radiation to a sample when activated by the optical signal;
an terahertz receiver optically coupled to the to the optical source, the terahertz receiver configured to detect terahertz radiation conditioned by a sample and generate an electrical signal which can be interpreted, scaled and/or digitized by a data acquisition system electrically coupled to the terahertz receiver;
a means for providing the optical signal to both the terahertz transmitter and terahertz receiver such that the terahertz receiver is synchronized to the terahertz transmitter by the optical signal; and
wherein the means allows for the stretching an optical fiber carrying the optical signal provided to the terahertz transmitter and terahertz receiver such that the terahertz receiver is synchronized to the terahertz transmitter by the optical signal.

12. The system of claim 11, wherein the means further comprising:
a multiplexer optically coupled to the optical source;
an optical fiber optically coupled to the multiplexer;
wherein the multiplexer is configured to provide a first pulse based on the optical signal to the optical fiber;
wherein the multiplexer is configured to provide a second pulse based on the optical signal to the optical fiber;
wherein the first pulse and second pulse are orthogonal to each other as they travel through the optical fiber;
a demultiplexer optically coupled to the optical fiber, the demultiplexer configured to receive the first and second pulse and provide the first pulse to the terahertz transmitter and the second pulse the terahertz receiver.

13. The system of claim 11, wherein optical source further comprises a laser source configured to output optical pulses.

14. The system of claim 13, further comprising a compensator optically located between the laser source and the means for providing the optical signal to both the terahertz transmitter and terahertz receiver, wherein the compensator is configured to add opposite sign dispersion to optical pulses emitted by the laser source to correct for a stretching of the optical pulses as they travel through the means for providing the optical signal to both the terahertz transmitter and terahertz receiver.

15. The system of claim 14, further comprising an optical splitter optically located between the laser source and the means for providing the optical signal to both the terahertz transmitter and terahertz receiver, wherein the optical splitter is configured to spilt the optical signal and provide the split optical signals to the means for providing the optical signal to both the terahertz transmitter and terahertz receiver.

* * * * *

UNITED STATES PATENT AND TRADEMARK OFFICE
CERTIFICATE OF CORRECTION

PATENT NO.         : 8,436,310 B2                                                                Page 1 of 1
APPLICATION NO.    : 13/266023
DATED              : May 7, 2013
INVENTOR(S)        : David Zimdars It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 15 days.

Signed and Sealed this
Eighth Day of September, 2015

Michelle K. Lee
*Director of the United States Patent and Trademark Office*